United States Patent
Zachar

(10) Patent No.: US 10,173,022 B1
(45) Date of Patent: Jan. 8, 2019

(54) LARYNGEAL MASK CUFF

(71) Applicant: AIRWAY MEDIX S.A., Warsaw (PL)

(72) Inventor: Oron Zachar, Tel Aviv (IL)

(73) Assignee: AIRWAY MEDIX S.A., Warsaw (PL)

( * ) Notice: Subject to any disclaimer, the term of this patent is extended or adjusted under 35 U.S.C. 154(b) by 0 days.

(21) Appl. No.: 15/951,564

(22) Filed: Apr. 12, 2018

Related U.S. Application Data

(63) Continuation-in-part of application No. 15/878,993, filed on Jan. 24, 2018.

(60) Provisional application No. 62/592,020, filed on Nov. 29, 2017.

(51) Int. Cl.
*A61M 16/04* (2006.01)

(52) U.S. Cl.
CPC ...... *A61M 16/044* (2013.01); *A61M 16/0447* (2014.02); *A61M 2205/3341* (2013.01); *A61M 2210/1028* (2013.01)

(58) Field of Classification Search
None
See application file for complete search history.

(56) References Cited

U.S. PATENT DOCUMENTS

| | | | |
|---|---|---|---|
| 5,632,271 A | 5/1997 | Brain | |
| 6,439,232 B1 | 8/2002 | Brain | |
| 6,526,977 B1 | 3/2003 | Gobel | |
| 7,305,985 B2 | 12/2007 | Brain | |
| 8,783,256 B2 | 7/2014 | Brain | |
| 2003/0037790 A1 | 2/2003 | Brain | |
| 2008/0078403 A1 | 4/2008 | Clayton | |
| 2012/0145160 A1 | 6/2012 | Brain | |

(Continued)

FOREIGN PATENT DOCUMENTS

| | | |
|---|---|---|
| CN | 106823086 | 6/2017 |
| EP | 0922465 | 6/1999 |
| WO | 2015015233 | 2/2015 |

OTHER PUBLICATIONS

"Two-balloon experiment", Wikipedia, downloaded from https://en.wikipedia.org/wiki/Twoballoon_experiment on Jan. 22, 2018, total 4 pages.

(Continued)

*Primary Examiner* — Rachel T Sippel
(74) *Attorney, Agent, or Firm* — Sughrue Mion, PLLC

(57) ABSTRACT

A laryngeal mask airway (LMA) device includes an inflatable annular cuff, which, when disposed in free space, is characterized by a pressure-volume curve that represents the pressure in the cuff when inflated, from a deflated negative pressure, by different volumes of ambient-pressure air, which include a low-pressure volume that results in a low pressure of 10 cm H2O. The pressure-volume curve includes (a) a low-pressure-range average rate of change over a low-pressure volume interval between 1.0 and 1.2 times the low-pressure volume, (b) a medium-pressure-range average rate of change over a medium-pressure volume interval between 2.0 and 2.2 times the low-pressure volume, and (c) a medium pressure at a medium volume of the cuff equal to 2.0 times the low-pressure volume. The medium-pressure-range average rate of change is less than 0.5 times the low-pressure-range average rate of change, and the medium pressure is between 20 and 200 cm H2O.

20 Claims, 10 Drawing Sheets

(56) References Cited

U.S. PATENT DOCUMENTS

2016/0158040 A1* 6/2016 Zupkofska ............... A61F 2/82
623/23.7

OTHER PUBLICATIONS

Teleflex, LMA Supreme brochure, Mar. 2014, Total 2 pages.
Ambu, AuraOnce AuraStraight brochure, Feb. 2009, total 4 pages.
Rokamp Kim et al, "Tracheal tube and laryngeal maskcuff pressure during anaesthesia—mandatory monitoring is in need", BMC Anesthesiology, Dec. 2010 (text only), total 10 pages.
Teleflex, Quick-Reference-Guide LMA, 2013, total 2 pages.
U.S. Appl. No. 62/592,020, filed Nov. 29, 2017.
Legend M.D. product catalog excerpts 2007.
An Office Action dated May 2, 2018, which issued during the prosecution of U.S. Appl. No. 15/878,993.
Communication dated Jul. 6, 2018 issued by the United States Patent and Trademark Office in U.S. Appl. No. 15/878,993.

* cited by examiner

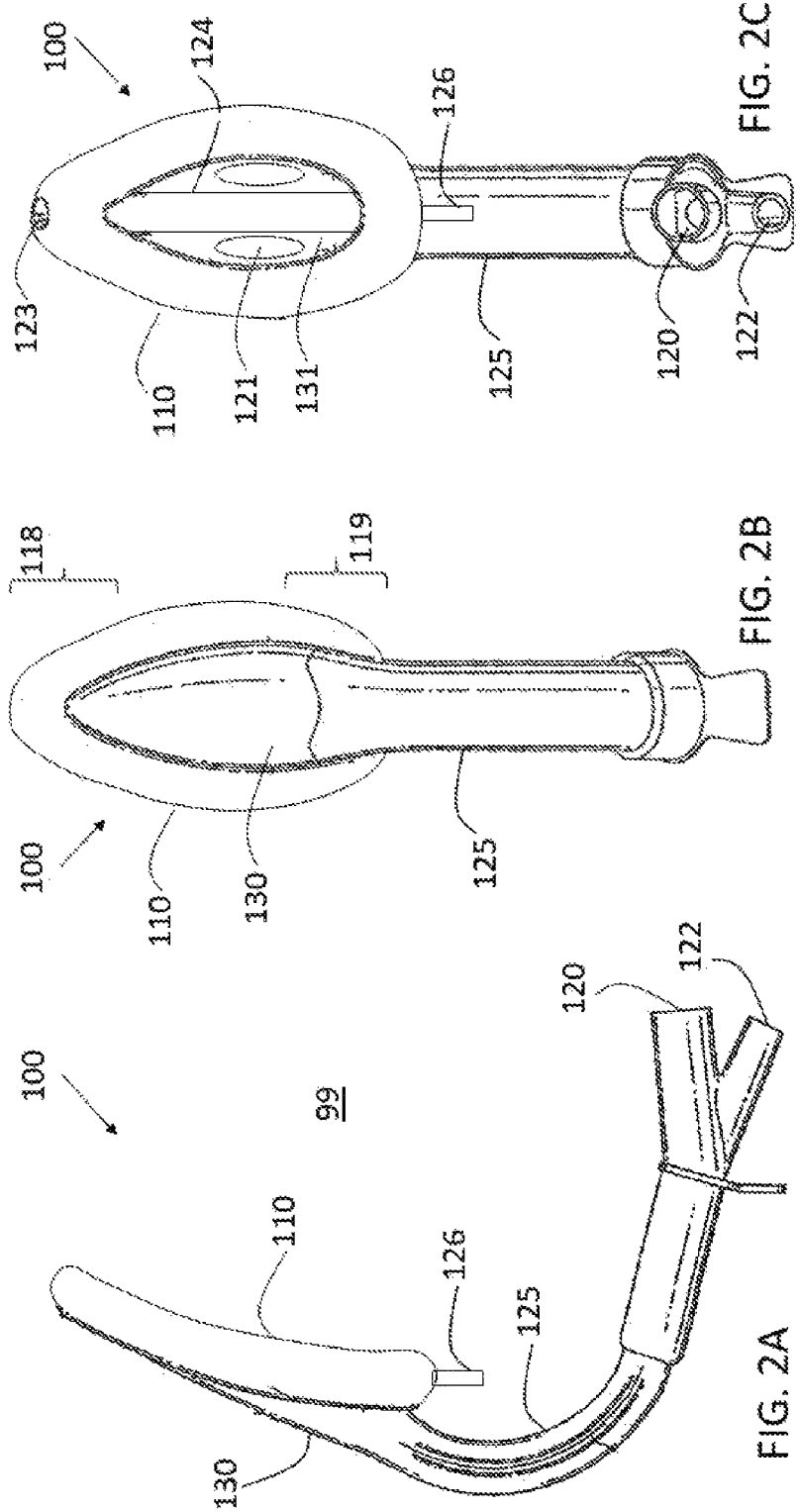

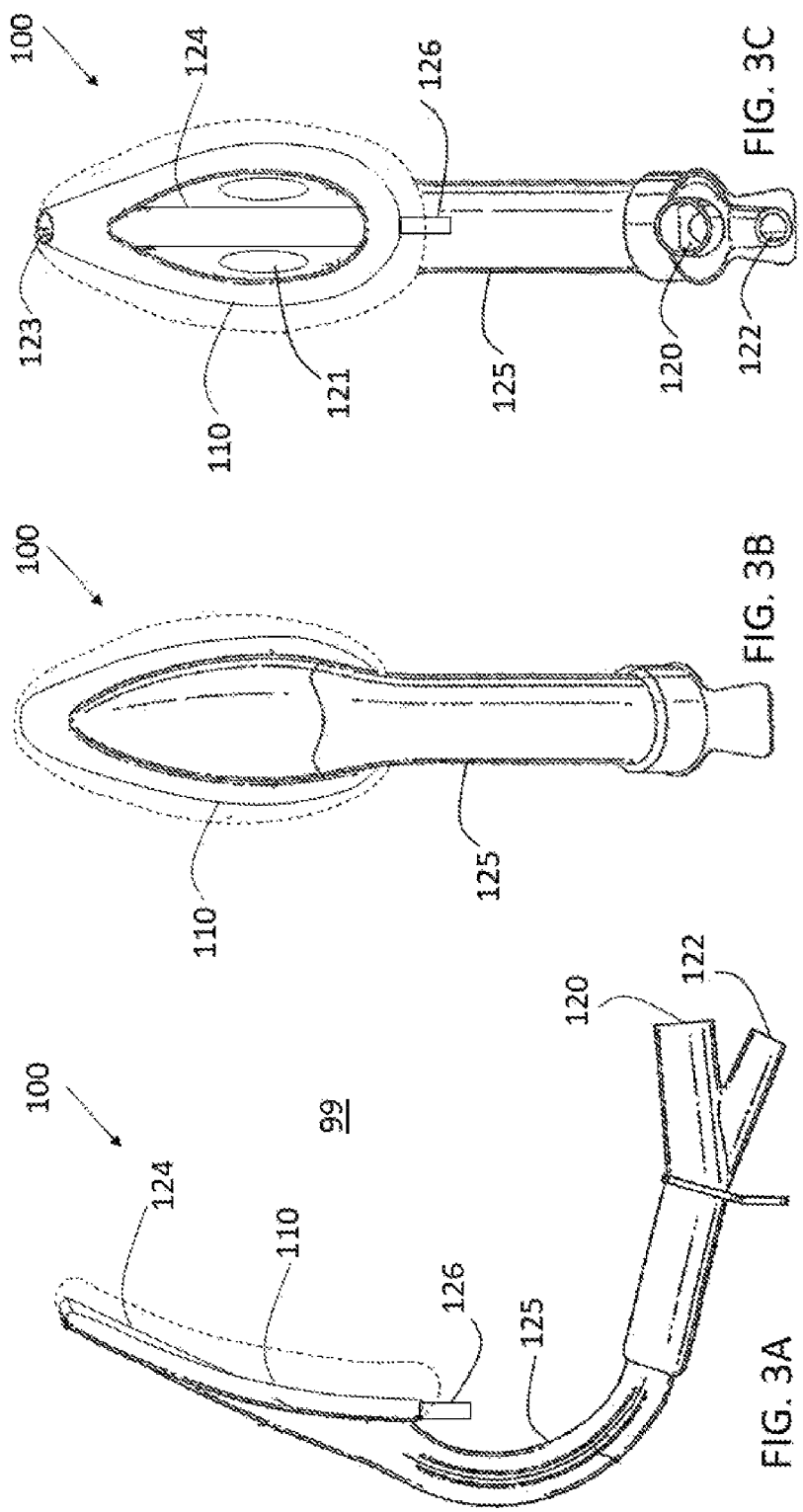

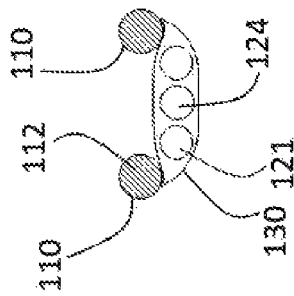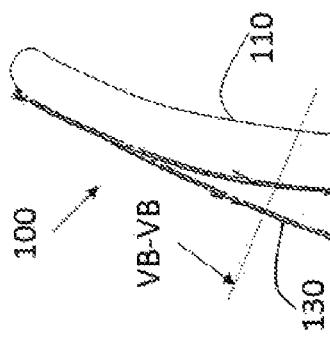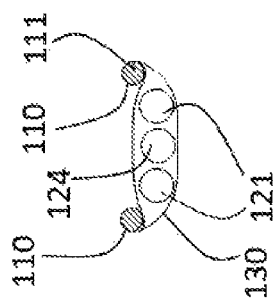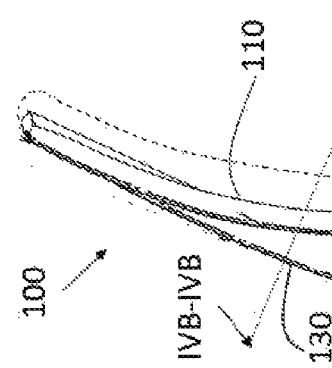

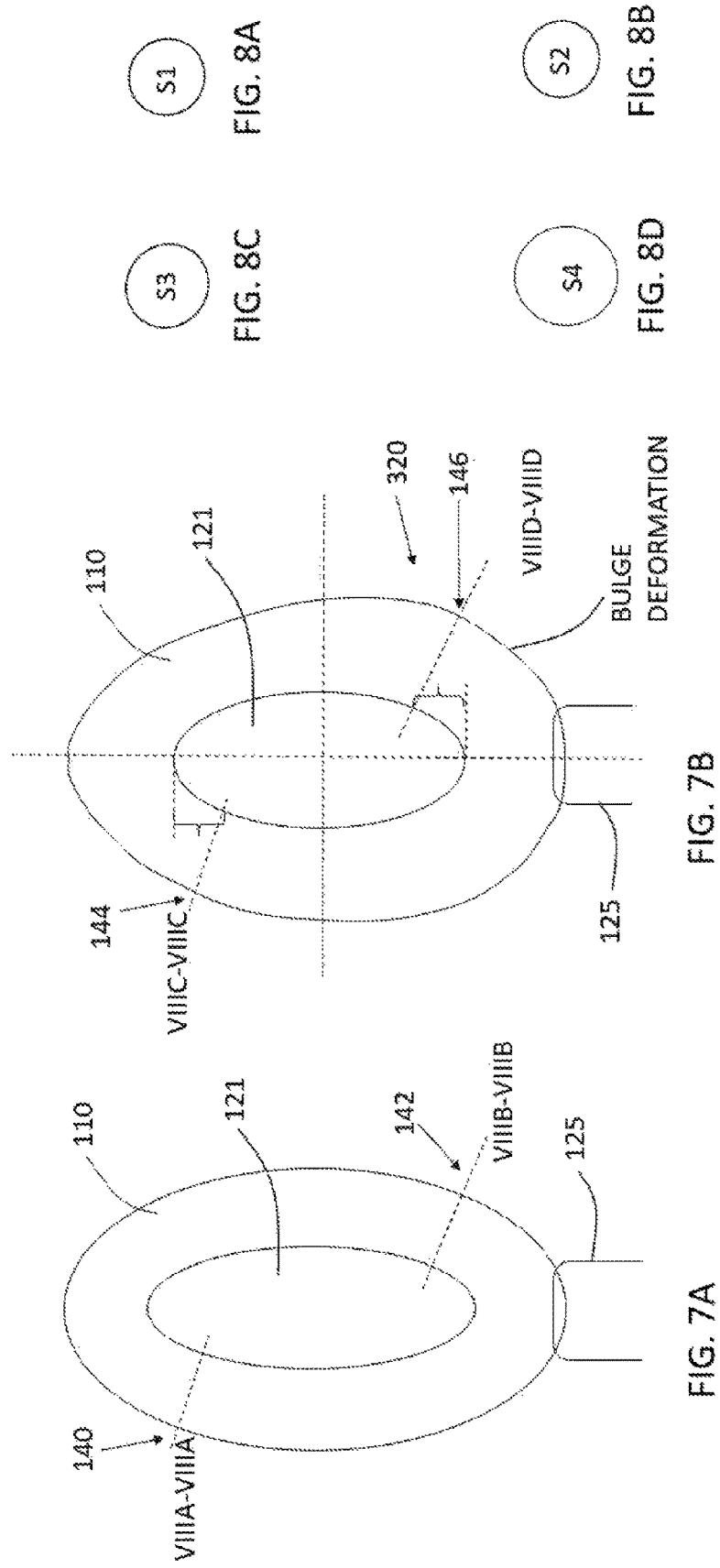

LARYNGEAL MASK CUFF

CROSS-REFERENCE TO RELATED APPLICATIONS

The present application is a continuation-in-part of U.S. application Ser. No. 15/878,993, filed Jan. 24, 2018, which claims the benefit of U.S. Provisional Application 62/592,020, filed Nov. 29, 2017. All of these applications are assigned to the assignee of the present application and are incorporated herein by reference.

FIELD OF THE APPLICATION

The present invention relates generally to lung ventilation devices, and specifically to laryngeal mask airway devices (LMA devices).

BACKGROUND OF THE APPLICATION

Laryngeal mask airway devices (LMA devices) are useful in facilitating lung ventilation by forming a low-pressure seal around the patient's laryngeal inlet, thereby avoiding the known harmful effects of endotracheal tube (ETT) devices, which form a seal within the trachea. LMA devices have become standard medical devices, instead of ETT devices, for rapidly and reliably establishing an unobstructed airway in a patient in emergency situations and in the administration of anesthetic gases. Some LMA devices further include a drainage tube, which opens into the distal tip of the mask and emerges from the mouth of the patient.

During general anesthesia, pulmonary ventilation is secured with an ETT device or by a LMA device, and attention to the risk of complications related to a high intracuff pressure is important. When the cuff-to-tracheal wall pressure exceeds the tracheal capillary pressure (130-140 cm H2O) for approximately 15 minutes, the tracheal mucous membrane becomes ischemic. The intracuff pressure approximates the cuff-to-tracheal wall pressures in high volume/low pressure cuffs, and a cuff pressure below 120 cm H2O is recommended to prevent ischemic injury. In addition, recurrent laryngeal nerve palsy has been demonstrated in up to 5% of patients after intubation, and a high cuff pressure is suspected as contributing to this complication. Similarly, in patients provided with a laryngeal mask, a high cuff pressure may lead to palsy of the lingual, hypoglossal, and recurrent laryngeal nerves, and postoperative sore throat.

The risk during anesthesia with nitrous oxide (NO) is further complicated by the fact that NO gases penetrate the cuff, thereby gradually increasing the cuff pressure above the initial setting at which the cuff was inflated.

U.S. Pat. Nos. 8,783,256, 5,632,271, and 7,305,985, all to Brain, describe laryngeal mask airway devices.

Rokamp K Z et al., in "Tracheal tube and laryngeal mask cuff pressure during anaesthesia—mandatory monitoring is in need," BMC Anesthesiology December 2010 10:20, describe "a prospective quality-control study," in which "201 patients undergoing surgery during anaesthesia (without the use of nitrous oxide) were included for determination of the cuff pressure of the tracheal tubes and laryngeal masks" (abstract).

A "Quick Reference Guide," Teleflex (Triangle Park, NC, USA), 2013, lists various LMA Airways, having different sizes and maximum cuff volumes.

SUMMARY OF THE APPLICATION

Embodiments of the present invention provide a laryngeal mask airway (LMA) device, which comprises an inflatable annular cuff that is insertable through a mouth of a patient to an inserted location within the patient, such that an anterior side of the cuff forms a seal around a laryngeal inlet of the patient upon inflation of the cuff. When the cuff is inflated to a working medium pressure, the LMA device is suitable for facilitating lung ventilation. For example, the working medium pressure may be between 20 and 200 cm H2O, such as between 20 and 120 cm H2O, e.g., between 20 and 70 cm H2O, such as between 20 and 40 cm H2O.

The cuff, when disposed in free space, is characterized by a pressure-volume curve, which represents the pressure in the cuff when inflated, from a deflated negative pressure (e.g., −30 cm H2O), to different volumes of ambient-pressure air, which include a low-pressure volume that results in a low pressure of 10 cm H2O. The pressure-volume curve includes:
- a low-pressure-range average rate of change over a low-pressure volume interval between 1.0 and 1.2 times the low-pressure volume,
- a medium-pressure-range average rate of change over a medium-pressure volume interval between 2.0 and 2.2 times the low-pressure volume, and
- a medium pressure at a medium volume of the cuff equal to 2.0 times the low-pressure volume.

For some applications, the medium-pressure-range average rate of change is less than 0.5 times the low-pressure-range average rate of change, such as less than 0.4 times, or less than 0.2 times, the low-pressure-range average rate of change. Alternatively or additionally, for some applications, the medium-pressure-range average rate of change is between 1 and 25 cm H2O, such as between 5 and 20 cm H2O, e.g., between 10 and 20 cm H2O.

In order to provide the pressure-volume curve described above, the cuff comprises a highly elastic material that results in substantial expansion of the cuff upon incremental inflation. For example, the cuff may comprise non-latex synthetic polyisoprene, e.g., primarily non-latex synthetic polyisoprene by weight; for some applications, the average thickness of a wall of the cuff is between 0.5 and 1.5 mm, such as between 0.6 and 0.9 mm, at all non-attached locations of the cuff that are not attached to a backplate of the LMA device.

By contrast, conventional LMA devices employ cuffs having little elasticity at the working inflation pressure range.

As a result of the above-mentioned properties, the LMA device of the present invention has good tissue-conforming properties and low sensitivity to cuff inflation volume variations. The cuff of the present invention creates a good seal even at lower cuff pressures. The cuff pressure is less sensitive to restriction by boundary tissue contours than are conventional LMA cuffs. In addition, at working pressures, increases in inflation volume result predominantly in inflation of cuff regions with lower sealing pressure, thereby improving the seal in the most needed locations around the cuff perimeter.

By contrast, conventional LMA cuffs generally can establish a good seal with surrounding tissue only at high cuff pressure; as a result, recommended cuff pressures generally are above 50 cm H2O. This high pressure substantially limits the duration of ventilation with conventional LMA devices, in order to avoid a high risk of soft tissue ischemia. Moreover, in conventional LMA cuffs even small increases in inflation with ambient-pressure air result in large increases in pressure in the cuffs. Experiments conducted by the inventor demonstrated that the recommended "upper volume limits" of inflation of conventional LMA cuffs result in a cuff pressure greater than 100 cm H2O, which would put patients at risk of soft tissue ischemia within as little as 30 minutes.

In addition, since conventional LMA cuffs comprise low-compliance materials, adult-size LMA devices have a large pre-inflation cuff tube diameter in the range of 12 to 16 mm. Because conventional cuffs have little compliance, their cross-sectional area and volume increases by less than 25% when inflated to any working pressure between 20 and 60 cm H2O compared with the cross-sectional area and volume at a low pressure of 10 cm H2O. Conventional cuffs do not conform to the oral cavity tissue contours, but instead are pushed by the oral cavity to increase the cuff pressure further and simultaneously generate high pressure on particular tissue contours while having low sealing pressures on other portions of the oral cavity tissue.

There is therefore provided, in accordance with an Inventive concept 1 of the present application, a laryngeal mask airway (LMA) device including:

an inflatable annular cuff, which is insertable through a mouth of a patient to an inserted location within the patient, such that an anterior side of the cuff forms a seal around a laryngeal inlet of the patient upon inflation of the cuff;

a backplate attached to the cuff; and an airway tube having (a) a proximal end that is configured to be disposed outside the patient's mouth when the cuff is at the inserted location, and (b) a distal end that is in fluid communication with a port of the backplate, wherein the port is open through a hollow center of the annular cuff, wherein the cuff, when disposed in free space, is characterized by a pressure-volume curve that represents the pressure in the cuff when inflated, from a deflated negative pressure, by different volumes of ambient-pressure air, which include a low-pressure volume that results in a low pressure of 10 cm H2O, wherein the pressure-volume curve includes:

a low-pressure-range average rate of change over a low-pressure volume interval between 1.0 and 1.2 times the low-pressure volume, a medium-pressure-range average rate of change over a medium-pressure volume interval between 2.0 and 2.2 times the low-pressure volume, and a medium pressure at a medium volume of the cuff equal to 2.0 times the low-pressure volume, wherein the medium-pressure-range average rate of change is less than 0.5 times the low-pressure-range average rate of change, and wherein the medium pressure is between 20 and 200 cm H2O.

Inventive concept 2. The LMA device according to Inventive concept 1, wherein the medium pressure is between 20 and 120 cm H2O.

Inventive concept 3. The LMA device according to Inventive concept 2, wherein the medium pressure is between 20 and 70 cm H2O.

Inventive concept 4. The LMA device according to Inventive concept 3, wherein the medium pressure is between 20 and 40 cm H2O.

Inventive concept 5. The LMA device according to Inventive concept 1, wherein the medium-pressure-range average rate of change is equal to less than 0.4 times the low-pressure-range average rate of change.

Inventive concept 6. The LMA device according to Inventive concept 5, wherein the medium-pressure-range average rate of change is equal to less than 0.2 times the low-pressure-range average rate of change.

Inventive concept 7. The LMA device according to Inventive concept 1, wherein the low-pressure-range average rate of change is between 15 and 100 cm H2O.

Inventive concept 8. The LMA device according to Inventive concept 7, wherein the low-pressure-range average rate of change is between 20 and 50 cm H2O.

Inventive concept 9. The LMA device according to Inventive concept 1, wherein the pressure-volume curve does not have any local maximums at any volumes less than 3 times the low-pressure volume.

Inventive concept 10. The LMA device according to Inventive concept 1, wherein the cuff is configured such that when disposed in free space and inflated, from the deflated negative pressure, by the low-pressure volume, further inflation of the cuff with an incremental quantity of air results in a pressure in the cuff that is less than 25 cm H2O, the incremental quantity of air having a volume, when the air is at ambient pressure, equal to 10% of the low-pressure volume.

Inventive concept 11. The LMA device according to Inventive concept 1, wherein the cuff is configured such that when disposed in free space and inflated, from the deflated negative pressure, by the low-pressure volume, further inflation of the cuff with an incremental quantity of air results in a pressure in the cuff that is less than 35 cm H2O, the incremental quantity of air having a volume, when the air is at ambient pressure, equal to 20% of the low-pressure volume.

Inventive concept 12. The LMA device according to any one of Inventive concepts 1-11, wherein the medium-pressure-range average rate of change is between 1 and 25 cm H2O.

Inventive concept 13. The LMA device according to Inventive concept 12, wherein the medium-pressure-range average rate of change is between 5 and 20 cm H2O.

Inventive concept 14. The LMA device according to Inventive concept 13, wherein the medium-pressure-range average rate of change is between 10 and 20 cm H2O.

Inventive concept 15. The LMA device according to any one of Inventive concepts 1-11, wherein the cuff includes a material selected from the group of materials consisting of: non-latex synthetic polyisoprene and silicone.

Inventive concept 16. The LMA device according to Inventive concept 15, wherein the cuff includes the non-latex synthetic polyisoprene.

Inventive concept 17. The LMA device according to Inventive concept 16, wherein the cuff includes primarily non-latex synthetic polyisoprene by weight.

Inventive concept 18. The LMA device according to any one of Inventive concepts 1-11, wherein an average wall thickness of the cuff is between 0.5 and 1.5 mm at all non-attached locations of the cuff that are not attached to the backplate.

Inventive concept 19. The LMA device according to Inventive concept 18, wherein the average wall thickness is between 0.6 and 0.9 mm at all the non-attached locations of the cuff.

Inventive concept 20. The LMA device according to any one of Inventive concepts 1-11, wherein the cuff is configured, when disposed in free space and inflated, from the deflated negative pressure, by the low-pressure volume, to have an asymmetric toroidal tubular shape.

Inventive concept 21. The LMA device according to Inventive concept 20, wherein the cuff is configured, when disposed in free space and inflated, from the inflated negative pressure, by the low-pressure volume, to have an average low-pressure external cross-sectional area, measured locally perpendicular to the center line of the cuff, that is less than 225 mm2.

Inventive concept 22. The LMA device according to Inventive concept 21, wherein the average low-pressure external cross-sectional area is less than 81 mm2.

Inventive concept 23. The LMA device according to Inventive concept 20, wherein the cuff is configured, when disposed in free space and inflated, from the inflated negative pressure, by a volume of ambient-pressure air equal to 1.2 times the low-pressure volume, to have (a) a low-volume greatest external cross-sectional area and a low-volume smallest external cross-sectional area at respective locations around the cuff, and (b) a low-volume deformation ratio equal to the quotient of the low-volume greatest external cross-sectional area divided by the low-volume smallest external cross-sectional area, wherein the cuff is configured, when disposed in free space and inflated, from the deflated negative pressure, by a volume of ambient-pressure air equal to 3.0 times the low-pressure volume, to have (a) a high-volume greatest external cross-sectional area and a high-volume smallest external cross-sectional area at respective locations around the cuff, and (b) a high-volume deformation ratio equal to the quotient of the high-volume greatest external cross-sectional area divided by the high-volume smallest external cross-sectional area, wherein all of the external cross-sectional areas are measured locally perpendicular to a center line of the cuff, and wherein the high-volume deformation ratio equals at least 1.5 times the low-volume deformation ratio.

There is further provided, in accordance with an Inventive concept 24 of the present application, a laryngeal mask airway (LMA) device including:

an inflatable annular cuff, which is insertable through a mouth of a patient to an inserted location within the patient, such that an anterior side of the cuff forms a seal around a laryngeal inlet of the patient upon inflation of the cuff;

a backplate attached to the cuff; and an airway tube having (a) a proximal end that is configured to be disposed outside the patient's mouth when the cuff is at the inserted location, and (b) a distal end that is in fluid communication with a port of the backplate, wherein the port is open through a hollow center of the annular cuff, wherein the cuff, when disposed in free space, is characterized by a pressure-volume curve that represents the pressure in the cuff when inflated, from a deflated negative pressure, by different volumes of ambient-pressure air, which include a low-pressure volume that results in a low pressure of 10 cm H2O, wherein the pressure-volume curve includes:

a medium-pressure-range average rate of change over a medium-pressure volume interval between 2.0 and 2.2 times the low-pressure volume, wherein the medium-pressure-range average rate of change is between 1 and 25 cm H2O, and a medium pressure at a medium volume of the cuff equal to 2.0 times the low-pressure volume, wherein the medium pressure is between 20 and 200 cm H2O.

Inventive concept 25. The LMA device according to Inventive concept 24, wherein the medium-pressure-range average rate of change is between 5 and 20 cm H2O.

Inventive concept 26. The LMA device according to Inventive concept 25, wherein the medium-pressure-range average rate of change is between 10 and 20 cm H2O.

Inventive concept 27. The LMA device according to Inventive concept 24, wherein the medium pressure is between 20 and 120 cm H2O.

Inventive concept 28. The LMA device according to Inventive concept 27, wherein the medium pressure is between 20 and 70 cm H2O.

Inventive concept 29. The LMA device according to Inventive concept 28, wherein the medium pressure is between 20 and 40 cm H2O.

Inventive concept 30. The LMA device according to Inventive concept 24, wherein the pressure-volume curve does not have any local maximums at any volumes less than 3 times the low-pressure volume.

Inventive concept 31. The LMA device according to Inventive concept 24, wherein the cuff is configured such that when disposed in free space and inflated, from the deflated negative pressure, by the low-pressure volume, further inflation of the cuff with an incremental quantity of air results in a pressure in the cuff that is less than 25 cm H2O, the incremental quantity of air having a volume, when the air is at ambient pressure, equal to 10% of the low-pressure volume.

Inventive concept 32. The LMA device according to Inventive concept 24, wherein the cuff is configured such that when disposed in free space and inflated, from the deflated negative pressure, by the low-pressure volume, further inflation of the cuff with an incremental quantity of air results in a pressure in the cuff that is less than 35 cm H2O, the incremental quantity of air having a volume, when the air is at ambient pressure, equal to 20% of the low-pressure volume.

Inventive concept 33. The LMA device according to any one of Inventive concepts 24-32, wherein the cuff includes a material selected from the group of materials consisting of: non-latex synthetic polyisoprene and silicone.

Inventive concept 34. The LMA device according to Inventive concept 33, wherein the cuff includes the non-latex synthetic polyisoprene.

Inventive concept 35. The LMA device according to Inventive concept 34, wherein the cuff includes primarily non-latex synthetic polyisoprene by weight.

Inventive concept 36. The LMA device according to any one of Inventive concepts 24-32, wherein an average wall thickness of the cuff is between 0.5 and 1.5 mm at all non-attached locations of the cuff that are not attached to the backplate.

Inventive concept 37. The LMA device according to Inventive concept 36, wherein the average wall thickness is between 0.6 and 0.9 mm at all the non-attached locations of the cuff.

Inventive concept 38. The LMA device according to any one of Inventive concepts 24-32, wherein the cuff is configured, when disposed in free space and inflated, from the deflated negative pressure, by the low-pressure volume, to have an asymmetric toroidal tubular shape.

Inventive concept 39. The LMA device according to Inventive concept 38, wherein the cuff is configured, when disposed in free space and inflated, from the deflated negative pressure, by the low-pressure volume, to have an average low-volume external cross-sectional area, measured locally perpendicular to the center line of the cuff, that is less than 225 mm2.

Inventive concept 40. The LMA device according to Inventive concept 39, wherein the average low-volume external cross-sectional area is less than 81 mm2.

Inventive concept 41. The LMA device according to Inventive concept 38, wherein the cuff is configured, when disposed in free space and inflated, from the deflated negative pressure, by a volume of ambient-pressure air equal to 1.2 times the low-pressure volume, to have (a) a low-volume greatest external cross-sectional area and a low-volume smallest external cross-sectional area at respective locations around the cuff, and (b) a low-volume deformation ratio equal to the quotient of the low-volume greatest external cross-sectional area divided by the low-volume smallest external cross-sectional area, wherein the cuff is configured, when disposed in free space and inflated, from the deflated negative pressure, by a volume of ambient-pressure air equal to 3.0 times the low-pressure volume, to have (a) a high-volume greatest external cross-sectional area and a high-volume smallest external cross-sectional area at respective locations around the cuff, and (b) a high-volume deformation ratio equal to the quotient of the high-volume greatest external cross-sectional area divided by the high-volume smallest external cross-sectional area, wherein all of the external cross-sectional areas are measured locally perpendicular to a center line of the cuff, and wherein the high-volume deformation ratio equals at least 1.5 times the low-volume deformation ratio.

There is still further provided, in accordance with an Inventive concept 42 of the present application, a laryngeal mask airway (LMA) device including:

an inflatable annular cuff, which is insertable through a mouth of a patient to an inserted location within the patient, such that an anterior side of the cuff forms a seal around a laryngeal inlet of the patient upon inflation of the cuff;

a backplate attached to the cuff; and an airway tube having (a) a proximal end that is configured to be disposed outside the patient's mouth when the cuff is at the inserted location, and (b) a distal end that is in fluid communication with a port of the backplate, wherein the port is open through a hollow center of the annular cuff, wherein the cuff, is configured to have an asymmetric toroidal tubular shape when disposed in free space and inflated, from a deflated negative pressure, by a low-pressure volume of ambient-pressure air that results in a low pressure of 10 cm H2O in the cuff, wherein the cuff is configured, when disposed in free space and inflated, from the deflated negative pressure, by a volume of ambient-pressure air equal to 1.2 times the low-pressure volume, to have (a) a low-volume greatest external cross-sectional area and a low-volume smallest external cross-sectional area at respective locations around the cuff, and (b) a low-volume deformation ratio equal to the quotient of the low-volume greatest external cross-sectional area divided by the low-volume smallest external cross-sectional area, wherein the cuff is configured, when disposed in free space and inflated, from the deflated negative pressure, by a volume of ambient-pressure air equal to 3.0 times the low-pressure volume, to have (a) a high-volume greatest external cross-sectional area and a high-volume smallest external cross-sectional area at respective locations around the cuff, and (b) a high-volume deformation ratio equal to the quotient of the high-volume greatest external cross-sectional area divided by the high-volume smallest external cross-sectional area, wherein all of the external cross-sectional areas are measured locally perpendicular to a center line of the cuff, and wherein the high-volume deformation ratio equals at least 1.5 times the low-volume deformation ratio.

Inventive concept 43. The LMA device according to Inventive concept 42, wherein the cuff is configured such that when deflated at a pressure of −30 cm H2O, the cuff has respective wall thicknesses at the respective locations around the cuff having the low-volume smallest external cross-sectional area and the low-volume greatest cross-section area, and the wall thicknesses vary by less than 10% of a larger of the wall thicknesses.

There is additionally provided, in accordance with an Inventive concept 44 of the present application, a laryngeal mask airway (LMA) device including:

an inflatable annular cuff, which is insertable through a mouth of a patient to an inserted location within the patient, such that an anterior side of the cuff forms a seal around a laryngeal inlet of the patient upon inflation of the cuff;

a backplate attached to the cuff; and an airway tube having (a) a proximal end that is configured to be disposed outside the patient's mouth when the cuff is at the inserted location, and (b) a distal end that is in fluid communication with a port of the backplate, wherein the port is open through a hollow center of the annular cuff, wherein the cuff, is configured to have an asymmetric toroidal tubular shape when disposed in free space and inflated, from a deflated negative pressure, by a low-pressure volume of ambient-pressure air that results in a low pressure of 10 cm H2O in the cuff, wherein the cuff is configured, when disposed in free space and inflated to a high volume that resulted in a pressure of 40 cm H2O, to have (a) a high-volume greatest external cross-sectional area and a high-volume smallest external cross-sectional area at respective locations around the cuff, and (b) a high-volume deformation ratio equal to the quotient of the high-volume greatest external cross-sectional area divided by the low-volume smallest external cross-sectional area, wherein the cuff is configured, when disposed in free space and inflated to the low pressure of 10 cm H2O, to have (a) a low-volume greater cross-sectional area at the same location around the cuff as the high-volume greatest external cross-sectional area, and a low-volume smaller cross-sectional area at the same location around the cuff as the high-volume smallest external cross-sectional area, and (b) a low-volume deformation ratio equal to the quotient of the low-volume greater external cross-sectional area divided by the low-volume smaller external cross-sectional area, wherein all of the external cross-sectional areas are measured locally perpendicular to a center line of the cuff, and wherein the high-volume deformation ratio equals at least 1.5 times the low-volume deformation ratio.

Inventive concept 45. The LMA device according to Inventive concept 44, wherein the cuff is configured such that when deflated at a pressure of −30 cm H2O, the cuff has respective wall thicknesses at the respective locations around the cuff having the low-volume smaller external cross-sectional area and the low-volume greater cross-section area, and the wall thicknesses vary by less than 10% of a larger of the wall thicknesses.

Inventive concept 46. The LMA device according to any one of Inventive concepts 42 and 44, wherein the cuff is configured, when disposed in free space and inflated, from the deflated negative pressure, by a volume of ambient-pressure air equal to 2.0 times the low-pressure volume, to have a medium pressure that is between 20 and 200 cm H2O.

Inventive concept 47. The LMA device according to Inventive concept 46, wherein the medium pressure is less than 120 cm H2O.

Inventive concept 48. The LMA device according to Inventive concept 47, wherein the medium pressure is less than 80 cm H2O.

Inventive concept 49. The LMA device according to any one of Inventive concepts 42 and 44, wherein the high-volume deformation ratio equals at least 2 times the low-volume deformation ratio.

Inventive concept 50. The LMA device according to any one of Inventive concepts 42 and 44, wherein, the cuff is configured such that when deflated at a pressure of −30 cm H2O, the cuff has respective wall thicknesses at the respective locations around the cuff having the high-volume smallest external cross-sectional area and the high-volume greatest cross-section area, and the wall thicknesses vary by less than 10% of a larger of the wall thicknesses.

Inventive concept 51. The LMA device according to any one of Inventive concepts 42 and 44, wherein the cuff includes a material selected from the group of materials consisting of: non-latex synthetic polyisoprene and silicone.

Inventive concept 52. The LMA device according to Inventive concept 51, wherein the cuff includes the non-latex synthetic polyisoprene.

Inventive concept 53. The LMA device according to Inventive concept 52, wherein the cuff includes primarily non-latex synthetic polyisoprene by weight.

Inventive concept 54. The LMA device according to any one of Inventive concepts 42 and 44, wherein an average wall thickness of the cuff is between 0.5 and 1.5 mm at all non-attached locations of the cuff that are not attached to the backplate.

Inventive concept 55. The LMA device according to Inventive concept 54, wherein the average wall thickness is between 0.6 and 0.9 mm.

Inventive concept 56. The LMA device according to any one of Inventive concepts 42 and 44, wherein the cuff is configured, when disposed in free space and inflated, from the deflated negative pressure, by the low-pressure volume, to have an average low-volume external cross-sectional area, measured perpendicular to the center line of the cuff, that is less than 225 mm2.

Inventive concept 57. The LMA device according to Inventive concept 56, wherein the average low-volume external cross-sectional area is less than 81 mm2.

There is yet additionally provided, in accordance with an Inventive concept 58 of the present application, a method including:

inserting an inflatable annular cuff of a laryngeal mask airway (LMA) device through a mouth of a patient to an inserted location within the patient, such that a proximal end of an airway tube of the LMA device is disposed outside the patient's mouth, and a distal end of the airway tube is in fluid communication with a port of a backplate of the LMA device attached to the annular cuff, wherein the port is open through a hollow center of the annular cuff; and inflating the cuff such that an anterior side of the cuff forms a seal around a laryngeal inlet of the patient, wherein the cuff, when disposed in free space, is characterized by a pressure-volume curve that represents the pressure in the cuff when inflated, from a deflated negative pressure, by different volumes of ambient-pressure air, which include a low-pressure volume that results in a low pressure of 10 cm H2O, wherein the pressure-volume curve includes:

a low-pressure-range average rate of change over a low-pressure volume interval between 1.0 and 1.2 times the low-pressure volume, a medium-pressure-range average rate of change over a medium-pressure volume interval between 2.0 and 2.2 times the low-pressure volume, and a medium pressure at a medium volume of the cuff equal to 2.0 times the low-pressure volume, wherein the medium-pressure-range average rate of change is less than 0.5 times the low-pressure-range average rate of change, and wherein the medium pressure is between 20 and 200 cm H2O.

There is also provided, in accordance with an Inventive concept 59 of the present application, a method including:

inserting an inflatable annular cuff of a laryngeal mask airway (LMA) device through a mouth of a patient to an inserted location within the patient, such that a proximal end of an airway tube of the LMA device is disposed outside the patient's mouth, and a distal end of the airway tube is in fluid communication with a port of a backplate of the LMA device attached to the annular cuff, wherein the port is open through a hollow center of the annular cuff; and inflating the cuff such that an anterior side of the cuff forms a seal around a laryngeal inlet of the patient, wherein the cuff, is configured to have an asymmetric toroidal tubular shape when disposed in free space and inflated, from a deflated negative pressure, by a low-pressure volume of ambient-pressure air that results in a low pressure of 10 cm H2O in the cuff, wherein the cuff is configured, when disposed in free space and inflated, from the deflated negative pressure, by a volume of ambient-pressure air equal to 1.2 times the low-pressure volume, to have (a) a low-volume greatest external cross-sectional area and a low-volume smallest external cross-sectional area at respective locations around the cuff, and (b) a low-volume deformation ratio equal to the quotient of the low-volume greatest external cross-sectional area divided by the low-volume smallest external cross-sectional area, wherein the cuff is configured, when disposed in free space and inflated, from the deflated negative pressure, by a volume of ambient-pressure air equal to 3.0 times the low-pressure volume, to have (a) a high-volume greatest external cross-sectional area and a high-volume smallest external cross-sectional area at respective locations around the cuff, and (b) a high-volume deformation ratio equal to the quotient of the high-volume greatest external cross-sectional area divided by the high-volume smallest external cross-sectional area, wherein all of the external cross-sectional areas are measured locally perpendicular to a center line of the cuff, and wherein the high-volume deformation ratio equals at least 1.5 times the low-volume deformation ratio.

The present invention will be more fully understood from the following detailed description of embodiments thereof, taken together with the drawings, in which:

BRIEF DESCRIPTION OF THE DRAWINGS

FIGS. 2A-C are schematic illustrations of respective views of the LMA device of FIG. 1 with a cuff thereof inflated to a working medium volume, in accordance with an application of the present invention;

FIGS. 3A-C are schematic illustrations of respective views of the LMA device of FIG. 1 with a cuff thereof inflated to a low-pressure volume, in accordance with an application of the present invention;

FIGS. 4A-B are schematic illustrations of the LMA device of FIG. 1 with a cuff thereof inflated at a low pressure, in accordance with an application of the present invention;

FIGS. 5A-B are schematic illustrations of the LMA device of FIG. 1 with a cuff thereof inflated at a working medium pressure, in accordance with an application of the present invention;

FIGS. 7A and 7B are schematic illustrations of configurations of a cuff of the LMA device of FIG. 1, in accordance with an application of the present invention;

FIGS. 8A and 8B are cross-sectional illustrations of the cuff of FIG. 7A taken along lines VIIIA-VIIIA and VIIIB-VIIIB, respectively, in accordance with an application of the present invention;

FIGS. 8C and 8D are cross-sectional illustrations of the cuff of FIG. 7B taken along lines VIIIC-VIIIC and VIIID-VIIID, respectively, in accordance with an application of the present invention;

DETAILED DESCRIPTION OF APPLICATIONS

Figure 1:
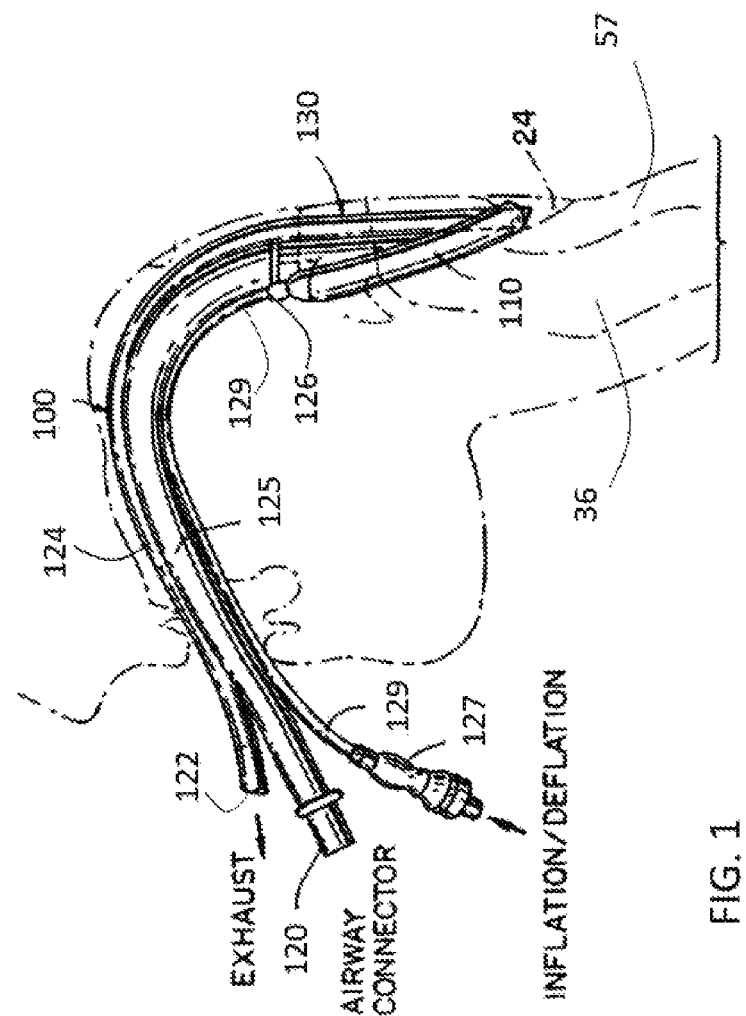
FIG. 1 is a schematic illustration of a laryngeal mask airway (LMA) device, in accordance with an application of the present invention.

FIG. 1 is a schematic illustration of a laryngeal mask airway (LMA) device 100, in accordance with an application of the present invention. In typical use, LMA device 100 is inserted into the throat while deflated (the upper surface of the throat is bounded by hard and soft palates). LMA device 100 is lodged in the pharynx at the base of the hypopharynx where the throat divides into the trachea 36 and the esophagus 57. Typically, after LMA device 100 is thus lodged in the pharynx, an inflatable annular cuff 110 of LMA device 100 is inflated at the inserted location with the patient, as illustrated in FIG. 1.

Reference is still made to FIG. 1 and is additionally made to FIGS. 2A-C, which are schematic illustrations of respective views of LMA device 100 with cuff 110 inflated to a working medium volume, as described hereinbelow with reference to FIGS. 5A-B, in accordance with an application of the present invention. FIGS. 2A, 2B, and 2C are side, posterior, and anterior views of LMA device 100, respectively.

Reference is yet additionally made to FIGS. 3A-C, which are schematic illustrations of respective views of LMA device 100 with cuff 110 inflated, from a deflated negative pressure, by a low-pressure volume V1, as described hereinbelow with reference to FIGS. 4A-B, in accordance with an application of the present invention. FIGS. 3A-C also show in phantom cuff 110 inflated to the working medium volume shown in FIGS. 2A-C.

LMA device comprises an airway tube 125, which is installed through the mouth of the patient. Airway tube 125 has a proximal end 120 that is configured to be disposed outside the patient's mouth when the cuff is at the inserted location. Proximal end 120 typically defines an airway connector port, which is configured for connection to air or other ventilating apparatus for the patient's lungs.

LMA device 100 further comprises a backplate 130 having an airway port 121 (shown in FIG. 2C) through which airway tube 125 can establish a free externally accessible ventilation passage, via the patient's mouth and throat, and past the epiglottis to the larynx. Airway tube 125 has a distal end that is in fluid communication with airway port 121. Airway port 121 is open through a hollow center of annular cuff 110. For example, backplate 130 may comprise an elastomer such as silicone rubber, PVC, or polyurethane, which may be the same material as or a different material from the cuff balloon, and may be relatively stiff due to its thickness of more than 1 mm. Backplate 130 typically has a one-piece, integral spoon-shape having an oval portion. Opposite sides of the oval portion are typically defined by a convex pharyngeal side and a concave laryngeal side. The periphery of the oval portion is hermetically bonded to the periphery of cuff 110, so as to establish, when placed within the human patient, separation between a laryngeal chamber region 131 and a pharyngeal region on the other side of backplate 130.

Inflatable annular cuff 110 is insertable through a mouth of a patient to an inserted location within the patient, typically when the cuff is deflated, such that an anterior side of the cuff forms a seal around a laryngeal inlet of the patient upon inflation of the cuff. Backplate 130 is attached to, and typically surrounded by, cuff 110. Optionally, backplate 130 is attached to cuff 110 at locations that are closer to a posterior side of the cuff than to an anterior side of the cuff. Optionally, backplate 130 is attached to cuff 110 only at locations on the posterior side of cuff 110. For some applications, LMA device 100 further comprises a drainage tube 124 extending from a distal drainage port 123 at a location near a distal end of cuff 110 to a proximal drainage port 122 at a location outside the patient's mouth when cuff 110 is at the inserted location.

LMA device 100 further comprises an externally-accessible inflation tube 129 and an inflation port 126 on cuff 110 for supplying air to the cuff and extracting air from (and therefore collapsing) the cuff, for inserting the cuff into and removing the cuff from the patient. Typically, an inflation check-valve 127 is disposed in inflation tube 129 for holding a given inflation of cuff 110. For some applications, inflation tube 129 comprises an inflation tube proximal port connector that comprises a male conical fitting with a taper. For some applications, the taper is at least a 5% taper. For some applications, the taper is a 6% taper, and the male conical fitting with the 6% taper complies with International Standard ISO 594-1:1986, which is the standard for connections to conventional inflation lumen proximal ports of LMA masks. Typically, though not necessarily, before cuff 110 is inserted to the patient, an inflation/deflation device is actuated to apply a vacuum, via inflation tube 129, to the interior of cuff 110 sufficient to fully deflate the cuff prior to insertion of the cuff through the mouth of the patient. For concreteness of discussion and test procedures, initial inflation volumes are assumed to start from a deflated state in which the cuff is deflated at suction pressure of negative 30 cm H2O (−30 cm H2O).

In the installed position shown in FIG. 1, a projecting but blunt distal region 118 (labeled in FIG. 2B) of cuff 110 is shaped so as to conform with the base of hypopharynx 24.

In some applications of the present invention, such as shown in FIGS. 2A-C, LMA device 100 is of the gastrolaryngeal mask (GLM) type, in which drainage tube 124 having a proximal drainage port 122 and a distal drainage port 123 (labeled in FIG. 2C), which enables extraction and external removal of gastric-discharge products from esophagus 57. Drainage tube 124 follows the general course of airway tube 125, provides sealed passage through the interior of cuff 110, and is open through distal region 118 of the cuff. Such GLM devices are commonly used in hospital settings in which evacuation suction sources are available, while simpler configurations of LMA devices without evacuation tubes are more commonly used in emergency intubations settings. Although the figures show drainage tube 124, drainage tube 124 is not an essential element of LMA device 100, and is not provided in some embodiments of the invention. Therefore, unless specifically stated to the contrary, all features of LMA device 100 described herein apply to LMA designs both with and without drainage tube 124.

Reference is now made to FIGS. 4A-B and 5A-B, which are schematic illustrations of LMA device 100 with cuff 110 inflated at a low pressure and a working medium pressure $P_M$, respectively, in accordance with an application of the present invention. FIGS. 4B and 5B are cross-sectional views take along lines IVB-IVB of FIG. 4A and VB-VB of FIG. 5A, respectively. FIG. 4A also shows in phantom cuff 110 inflated to the working medium volume shown in FIG. 5A.

When cuff 110 is inflated to the low pressure illustrated in FIGS. 4A-B, LMA device 100 is unsuitable for facilitating lung ventilation. For example, the low pressure may be 10 cm H2O. At this low pressure, cuff 110 has a first cross section 111, measured perpendicular to the center line of the cuff; the first cross section 111 has a first area. For some applications, cuff 110, when disposed in free space and inflated, from the deflated negative pressure, by the low-pressure volume V1 described hereinbelow with reference to FIGS. 6A-B, has an average low-volume external cross-sectional area, measured perpendicular to the center line of the cuff, that is less than 225 mm2, such as less than 144 mm2, e.g., less than 81 mm2.

As used in the present application, including in the claims, "disposed in free space" means disposed in ambient air 99 at atmospheric pressure at 20 degrees Celsius without being constrained by the patient's anatomy, a delivery tool, or anything else. As used in the present application, including in the claims, the "center line" of the cuff is the set of all centroids of transverse cross-sectional sections of the cuff along the cuff. Thus the cross-sectional sections are locally perpendicular to the center line, which runs along the cuff. (If the cuff is circular in cross-section, the centroids correspond with the centers of the circular cross-sectional sections.) In the present application, including in the claims, all pressures are gauge pressures that are zero-referenced against ambient air 99 pressure.

When cuff 110 is inflated to the working medium pressure $P_M$ illustrated in FIGS. 5A-B, LMA device 100 is suitable for facilitating lung ventilation. For example, the working medium pressure $P_M$ may be between 20 and 200 cm H2O, such as between 20 and 120 cm H2O, e.g., between 20 and 70 cm H2O, such as between 20 and 40 cm H2O. At the working medium pressure $P_M$, cuff 110 has a second cross section 112, measured perpendicular to the center line of the cuff; the second cross section 112 has a second area greater than the first area. Typically, cuff 110, when disposed in free space and inflated, from the deflated negative pressure, by the low-pressure volume V1 described hereinbelow with reference to FIGS. 6A-B, has an asymmetric toroidal tubular shape, generated, for example, by an asymmetrical oval or ellipse having a wider proximal 20% region 119 and narrower distal 20% region 118.

Figure 6A:
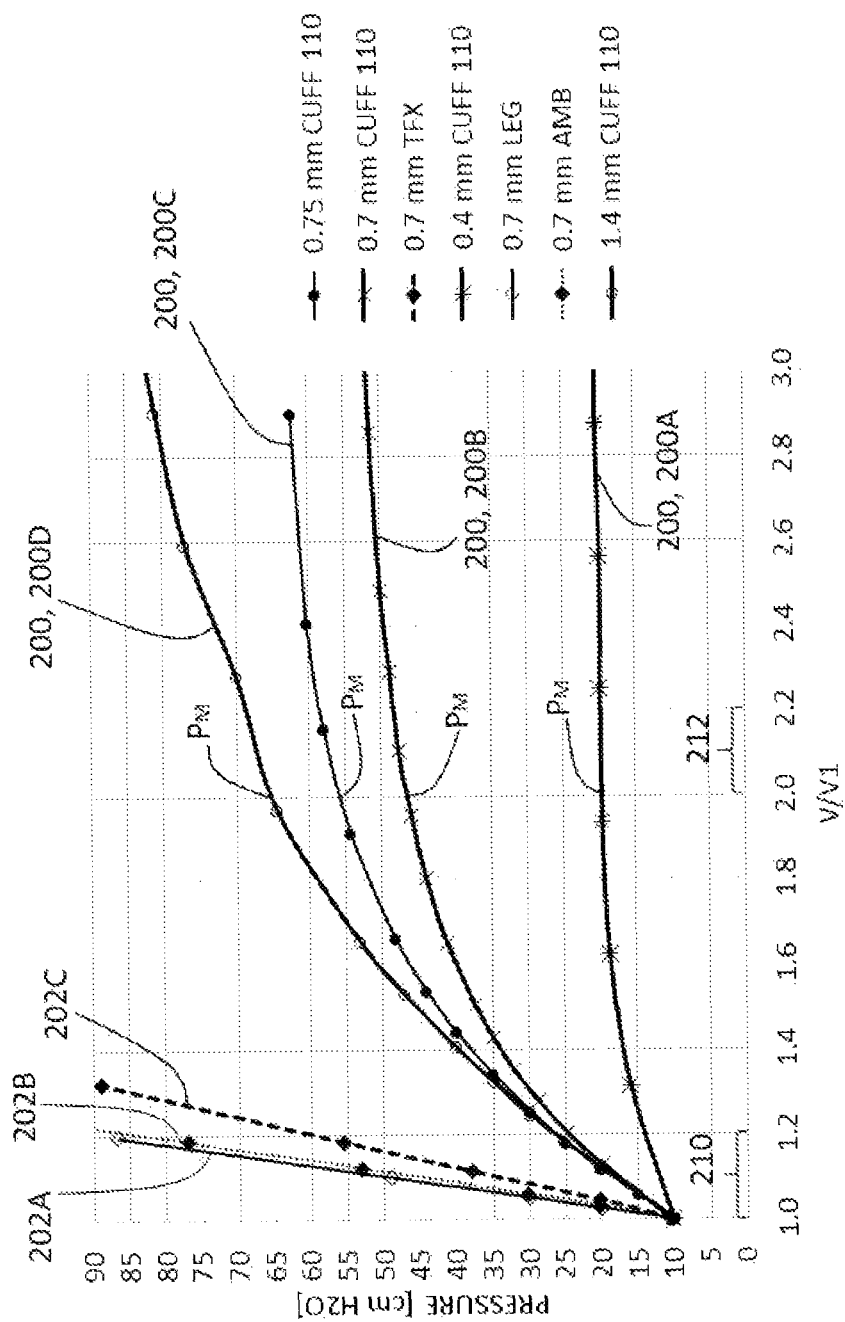
FIGS. 6A-B include several pressure-volume curves, some in accordance with an application of the present invention and others of devices in the prior art.
Figure 6B:
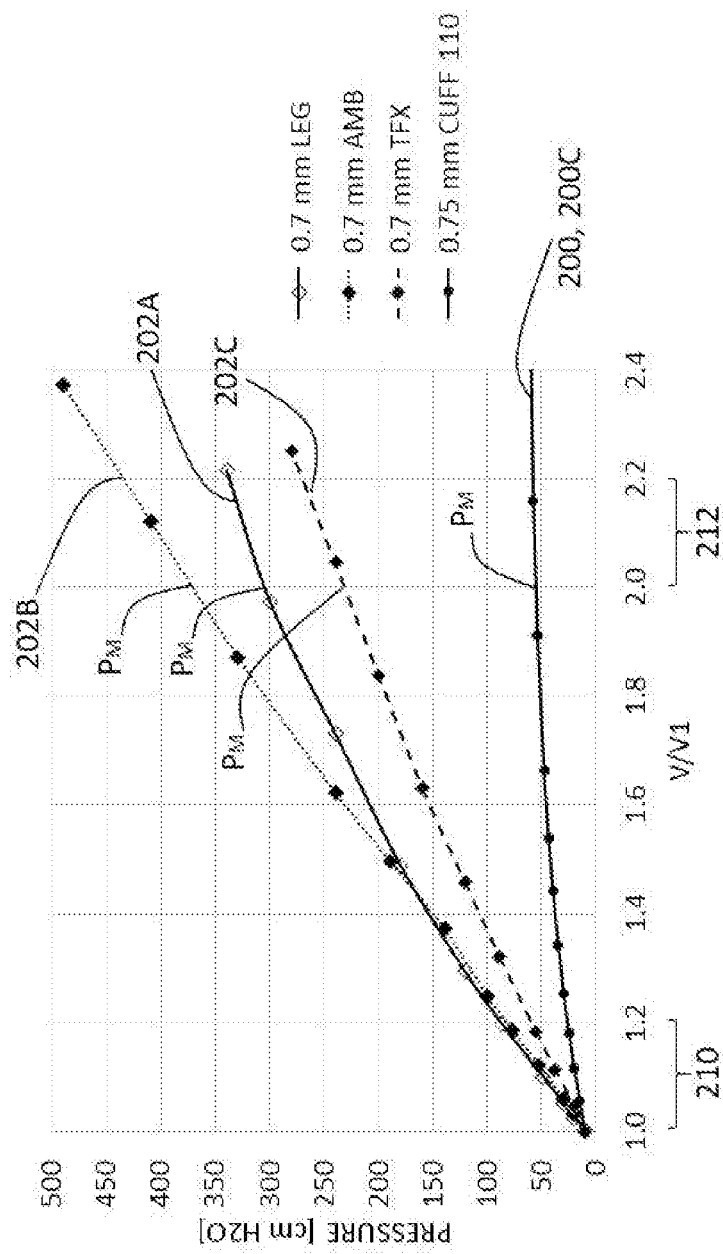

Reference is now made to FIGS. 6A-B, which include several pressure-volume curves 200, some in accordance with an application of the present invention and others of devices in the prior art. FIGS. 6A and 6B include different pressure ranges. Cuff 110, when disposed in free space, is characterized by a pressure-volume curve 200, which represents the pressure in cuff 110 when inflated, from a deflated negative pressure (e.g., −30 cm H2O), to different volumes of ambient-pressure air, which include a low-pressure volume V1 that results in a low pressure of 10 cm H2O. Pressure-volume curves 200 illustrated in FIG. 6A include exemplary pressure-volume curves 200A, 200B, 200C, and 200D, and in FIG. 6B include only exemplary pressure-volume curve 200C; a large number of additional pressure-volume curves having the general properties of pressure-volume curves 200 are possible, and are within the scope of the present invention. Exemplary pressure-volume curves 200A, 200B, 200C, and 200D are based on measurements made by the inventors using cuffs 110 having average wall thicknesses of 0.4 mm, 0.7 mm, 0.75 mm, and 1.4 mm, respectively. The low-pressure volumes V1 of air are defined as the quantities of ambient-pressure air added to cuff 110 when initially substantially empty of air, i.e., containing a negligible quantity of air when emptied at a deflated negative pressure of −30 cm H2O. These first volumes V1 served as baselines for comparison with pressures achieved upon additional inflation of the cuffs.

FIGS. 6A-B also include exemplary known pressure-volume curves 202A, 202B, and 202C, measured by the inventors using the following known LMA cuffs:
  pressure-volume curves 202A: a Legend M.D.™ LMA106 size #4 laryngeal mask device cuff (Legend Medical Devices, City of Industry, CA, USA), having an average wall thickness of 0.7 mm,
  pressure-volume curves 202B: an Ambu® AuraOnce™ size #4 laryngeal mask device cuff (Ambu A/S, Ballerup, Denmark), having an average wall thickness of 0.7 mm, and
  pressure-volume curves 202C: an LMA Supreme™ size #4 laryngeal mask device cuff (Teleflex Inc., Wayne, Pa., USA), having an average wall thickness of 0.7 mm.
Each of pressure-volume curves 200 includes:
  a low-pressure-range average rate of change over a low-pressure volume interval 210 between 1.0 and 1.2 times the low-pressure volume V1,
  a medium-pressure-range average rate of change over a medium-pressure volume interval 212 between 2.0 and 2.2 times the low-pressure volume V1, and
  a working medium pressure $P_M$ at a working medium volume of the cuff equal to 2.0 times the low-pressure volume V1.

In the present application, including in the claims, the "average rate of change" is the slope of the secant line joining respective points on the curve at the endpoints of the relevant interval, as is known in the mathematical arts.

For some applications, the medium-pressure-range average rate of change is less than 0.5 times the low-pressure-range average rate of change, such as less than 0.4 times, or less than 0.2 times, the low-pressure-range average rate of change.

Alternatively or additionally, for some applications, the medium-pressure-range average rate of change is between and 25 cm H2O, such as between 5 and 20 cm H2O, e.g., between 10 and 20 cm H2O. The low-pressure volume V1

(that results in the low pressure of 10 cm H2O) is typically about 20 cc (typically with a +/−5 cc variation range). Therefore, the average rate of change (i.e., slope) is divided by 20 to convert to physical inflation by cubic centimeters of air. As a result, in pressure-volume curves 200 a slope of 20 cm H2O is approximately an inflation rate of change of 1 cm H2O per cc of air inflation. This implies that movements of cuff 110 that compress or expand the cuff by +/−1 cc will result in only a small variation of the cuff pressure of +/−1 cm H2O. It is desired to avoid substantial changes in the cuff pressure, since high pressure can lead to patient soft tissue damage and low pressure compromises the air seal effectiveness for ventilating the patient. In contrast, conventional LMA cuffs, as demonstrated in the experimental data presented herein, have pressure-volume curves with average rates of changes (i.e., slopes) greater than 100 cm H2O, i.e., an approximate inflation a rate of change greater than 5 cm H2O per cc of air inflation.

For some applications, the low-pressure-range average rate of change is between 15 and 100 cm H2O, such as between 20 and 50 cm H2O.

Typically, the working medium pressure $P_M$ is between 20 and 200 cm H2O, such as between 20 and 120 cm H2O, e.g., between 20 and 70 cm H2O, such as between 20 and 40 cm H2O.

Typically, pressure-volume curve 200 does not have any local maximums at any volumes less than 3 times the low-pressure volume V1.

In order to provide pressure-volume curves 200 described above, cuff 110 comprises a highly elastic material that results in substantial expansion of the cuff upon incremental inflation. For example, cuff 110 may comprise non-latex synthetic polyisoprene, e.g., primarily non-latex synthetic polyisoprene by weight; for some applications, the average thickness of a wall of cuff 110 is between 0.5 and 1.5 mm, such as between 0.6 and 0.9 mm, at all non-attached locations of cuff 110 that are not attached to backplate 130. Alternatively, for example, cuff 110 may comprise silicone, e.g., primarily silicone by weight; for some applications, the average thickness of the wall of cuff 110 is between 0.5 and 1.5 mm, such as between 0.6 and 0.9 mm, at all non-attached locations of cuff 110 that are not attached to backplate 130; alternatively or additionally, for some applications, the silicone has a hardness of less than Shore A30, or less than Shore OO-80, or less than Shore OO-60.

By contrast, conventional LMA devices employ cuffs having little elasticity at the working inflation pressure range.

For some applications, cuff 110 is configured such that when disposed in free space and inflated, from the deflated negative pressure, by the low-pressure volume V1, further inflation of cuff 110 with an incremental quantity of air results in a pressure in cuff 110 that is less than 25 cm H2O, the incremental quantity of air having a volume, when the air is at ambient pressure, equal to 10% of the low-pressure volume V1.

For some applications, cuff 110 is configured such that when disposed in free space and inflated, from the deflated negative pressure, by the low-pressure volume V1, further inflation of cuff 110 with an incremental quantity of air results in a pressure in cuff 110 that is less than 35 cm H2O, the incremental quantity of air having a volume, when the air is at ambient pressure, equal to 20% of the low-pressure volume V1.

By contrast, cuff pressure in the known cuffs continuously increased with increases of inflation volume. At additional inflation volumes of as little as 20% of the respective first volumes V1, the pressures in the known cuffs rose to high levels that might cause soft tissue ischemia during ordinary use. This occurs because knowns cuffs substantially attain their working volumes at low inflation pressures, such as 10 cm H2O. Further inflation by an additional 10% to 30% of the inflation volume that resulted in the pressure of 10 cm H2O results in only a small increase of the cuff volume and a large increase (typically greater than 100%) in the cuff pressure.

Reference is still made to FIGS. 6A-B. During use of LMA device 100 after cuff 110 has been placed at the inserted location, as shown in FIG. 1, cuff 110 is ideally inflated to a pressure greater than 20 cm H2O (e.g., greater than 25 cm H2O, such as greater than 30 cm H2O) and less than 60 cm H2O.

In practice, the healthcare worker often inflates cuff 110 with a known quantity of ambient-pressure air, rather than to a certain pressure, because the pressure is typically not measured during or after inflation of cuff 110. Also, often the healthcare worker may inflate the cuff outside the patient's mouth and then press the cuff into the patient's throat. Consequently, in conventional devices, there are often significant pressure variations in the outcome of inflation pressure compared with the intended target pressure.

LMA device 100 is typically accompanied by instructions for use that specify a narrow range of quantities of ambient-pressure air, e.g., 25 to 30 cc for a standard adult-size cuff. The range of air quantities is ascertained by the manufacturer for each configuration of LMA device 100, based in large part on pressure-volume curve 200 of cuff 110. Ideally, the specified range of quantities of air would result in a fixed pressure volume range. However, in practice the variation in human throat size and shape results in substantial variation in the cuff's actual size when in place, and movement of the patient may shift the cuff's positioning within the throat. Yet, because of the shapes of pressure-volume curves 200 of cuff 110, moderate underinflation and even substantial over-inflation still results in a working medium pressure $P_M$ that is suitable for facilitating lung ventilation, without any need to adjust the inflation of the cuff.

As mentioned above, one of pressure-volume curves 200 characterizes cuff 110 when disposed in free space. Nevertheless, when the cuff is placed at the inserted location, the constraints of the anatomy on the cuff typically have only minimal impact on the pressure-volume curve of the cuff, and do not materially increase the pressure in the cuff. By contrast, in conventional LMA devices, such constraints generally lead to a significant increase (e.g., by more than 25%, or more than 50%) of the cuff pressure compared to pressure achieved at the same inflation volume when the cuff is disposed in free space.

As used in the present application, including in the claims, the terms "proximal" and "distal" refer to locations nearer to the operator and to the inside of the body, respectively.

Reference is now made to FIGS. 7A and 7B, which are schematic illustrations of configurations of cuff 110, in accordance with an application of the present invention. Reference is also made to FIGS. 8A and 8B, which are cross-sectional illustrations of the cuff of FIG. 7A taken along lines VIIIA-VIIIA and VIIIB-VIIIB, respectively, in accordance with an application of the present invention. Reference is further made to FIGS. 8C and 8D, which are cross-sectional illustrations of the cuff of FIG. 7B taken along lines VIIIC-VIIIC and VIIID-VIIID, respectively, in accordance with an application of the present invention.

In an experiment performed on behalf of the inventor, an implementation of cuff 110 was constructed and filled to different pressures. The experimental cuff had a pressure-volume curve similar to pressure-volume curve 200B, described hereinabove with reference to FIGS. 6A-B.

When disposed in free space, cuff 110 was first inflated, from the deflated negative pressure, by a volume of ambient-pressure air equal to 1.2 times the low-pressure volume V1, resulting in the cuff shape shown in FIG. 7A. As can be seen, at this level of inflation the cuff nearly retained its tubular shape. Cuff 110 had:
- a low-volume smallest external cross-sectional area S1, shown in cross section in FIG. 8A, at a first location 140 around cuff 110,
- a low-volume greatest external cross-sectional area S2, shown in cross section in FIG. 8B, at a second location 142 around cuff 110, and
- a low-volume deformation ratio equal to the quotient of the low-volume greatest external cross-sectional area S2 divided by the low-volume smallest external cross-sectional area S1.

When disposed in free space, cuff 110 was subsequently inflated, from the deflated negative pressure, by a volume of ambient-pressure air equal to 3.0 times the low-pressure volume V1, resulting in the cuff shape shown in FIG. 7B. As can be seen, at this level of inflation a deformation 320 formed. Cuff 110 had:
- a high-volume smallest external cross-sectional area S3, shown in cross section in FIG. 8C, at a third location 144 around cuff 110,
- a high-volume greatest external cross-sectional area S4, shown in cross section in FIG. 8D, at a fourth location 146 around cuff 110, and
- a high-volume deformation ratio equal to the quotient of the high-volume greatest external cross-sectional area S4 divided by the high-volume smallest external cross-sectional area S3.

All of the external cross-sectional areas were measured locally perpendicular to the center line of cuff 110. First location 140 and third location 144 may be the same or different from each other. Second location 142 and fourth location 146 may be the safe or different from each other.

In an application of the present invention, the high-volume deformation ratio equals at least 1.5 times the low-volume deformation ratio, such as at least 2 times the low-volume deformation ratio.

Figure 9A:
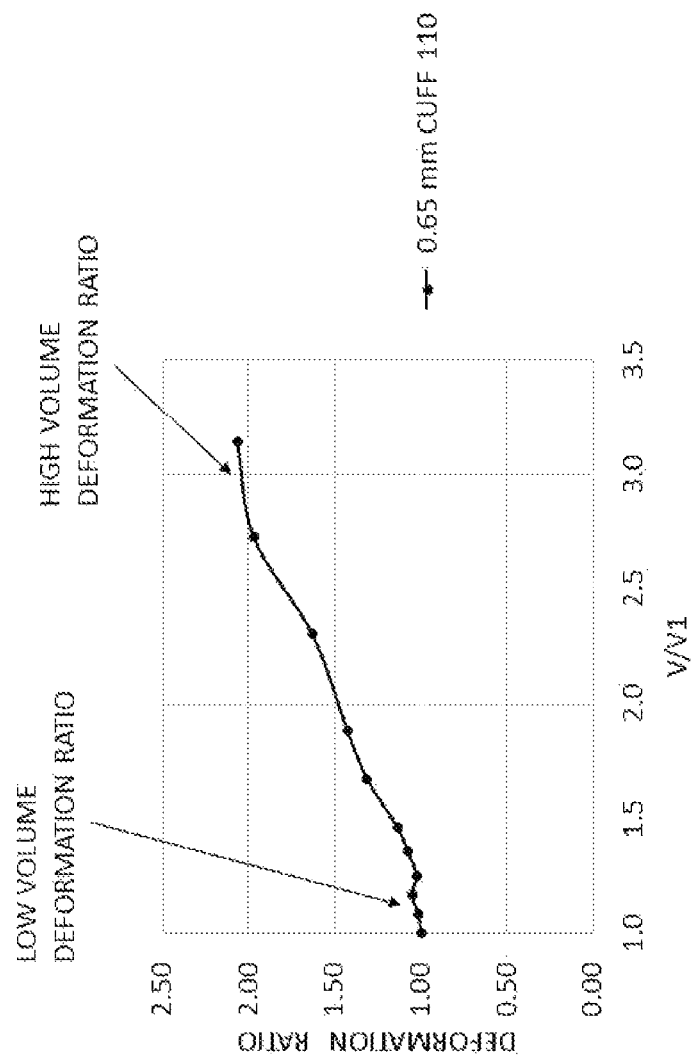
FIGS. 9A-B are graphs illustrating respective deformation ratios of a cuff of the LMA device of FIG. 1, calculated in accordance with an experiment performed on behalf the inventor.
Figure 9B:
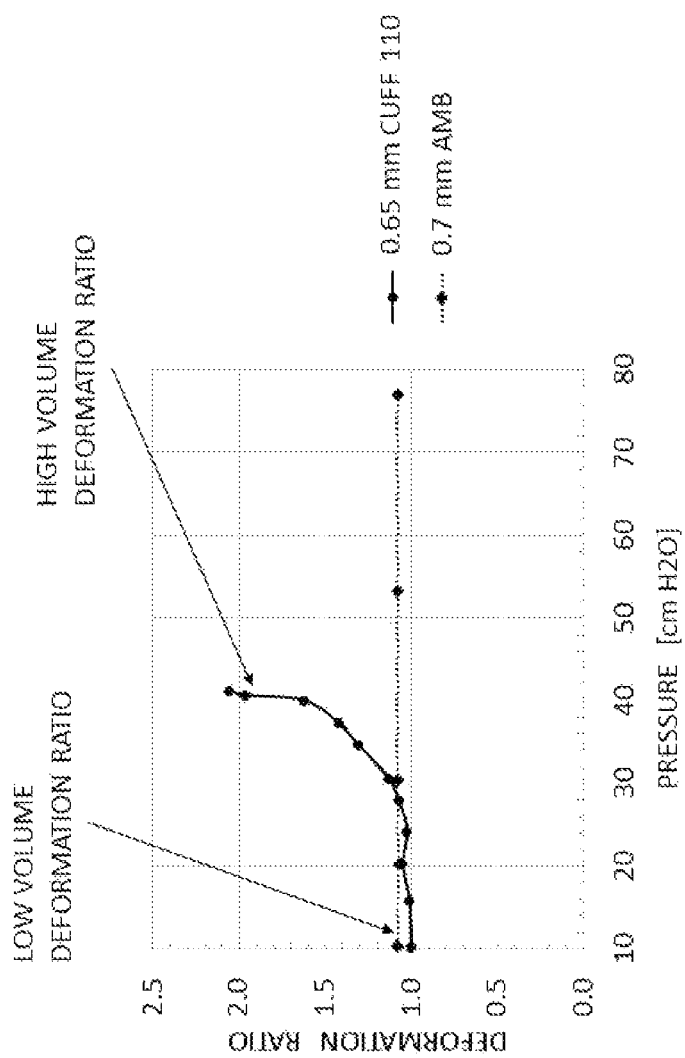

Reference is made to FIGS. 9A-B, which are graphs illustrating respective deformation ratios of cuff 110, calculated in accordance with an experiment performed on behalf the inventor, in accordance with an application of the present invention. The cuff used in the experiment had an average wall thickness of 0.65 mm.

The graph of FIG. 9A shows different high-volume deformation ratios of cuff 110 when cuff 110 was inflated, from the deflated negative pressure, by a volume of ambient-pressure air equal to different multiples of the low-pressure volume V1, such as described hereinabove with reference to FIGS. 7A-B and 8A-D. As described hereinabove with reference to FIGS. 7A-B and 8A-D, in an application of the present invention, the high-volume deformation ratio equals at least 1.5 times the low-volume deformation ratio, such as at least 2 times the low-volume deformation ratio.

The graph of FIG. 9B shows different high-volume deformation ratios of cuff 110 when cuff 110 was inflated to different pressures.

When disposed in free space, cuff 110 was inflated to a high volume that resulted in a pressure of 40 cm H2O, resulting in a cuff shape similar to that shown in FIG. 7B. As can be seen, at this level of inflation deformation 320 formed. Cuff 110 had:
- high-volume greatest external cross-sectional area S4 and high-volume smallest external cross-sectional area S3, at respective locations around cuff 110, and
- a high-volume deformation ratio equal to the quotient of the high-volume greatest external cross-sectional area S4 divided by the high-volume smallest external cross-sectional area S3.

In addition, when disposed in free space, cuff 110 was inflated to a low pressure of 10 cm H2O, resulting in a cuff shape similar to that shown in FIG. 7A. As can be seen, at this level of inflation the cuff nearly retained its tubular shape. Cuff 110 had:
- a low-volume smaller external cross-sectional area S1 at the same location around cuff 110 as the high-volume smallest external cross-sectional area S3,
- a low-volume greater external cross-sectional area S2 at the same location around cuff 110 as the high-volume greatest external cross-sectional area S4, and
- a low-volume deformation ratio equal to the quotient of the low-volume greater external cross-sectional area S2 divided by the low-volume smaller external cross-sectional area S1.

All of the external cross-sectional areas were measured locally perpendicular to the center line of cuff 110.

In an application of the present invention, the high-volume deformation ratio equals at least 1.5 times the low-volume deformation ratio, such as at least 2 times the low-volume deformation ratio.

Typically, cuff 110 is configured, when disposed in free space and inflated, from the deflated negative pressure, by a volume of ambient-pressure air equal to 2.0 times the low-pressure volume V1, to have a working medium pressure $P_M$ that is between 20 and 200 cm H2O, such as between 20 and 120 cm H2O, e.g., between 20 and 80 cm H2O.

Typically, cuff 110 is configured such that when deflated at a pressure of −30 cm H2O, cuff 110 has respective wall thicknesses at (a) third location 144 around cuff 110 having the high-volume smallest external cross-sectional area S3 and (b) fourth location 146 around cuff 110 having the high-volume greatest cross-section area S4, and the wall thicknesses vary by less than 10% of a larger of the wall thicknesses. (Cuff manufacturing processes typically result in variations in thickness of up to 10%.)

Typically, cuff 110 is configured such that when deflated at a pressure of −30 cm H2O, cuff 110 has respective wall thicknesses at (a) first location 140 around cuff 110 having the low-volume smallest external cross-sectional area S1 and (b) second location 142 around cuff 110 having the low-volume greatest cross-section area S2, and the wall thicknesses vary by less than 10% of a larger of the wall thicknesses.

Figure 10A:
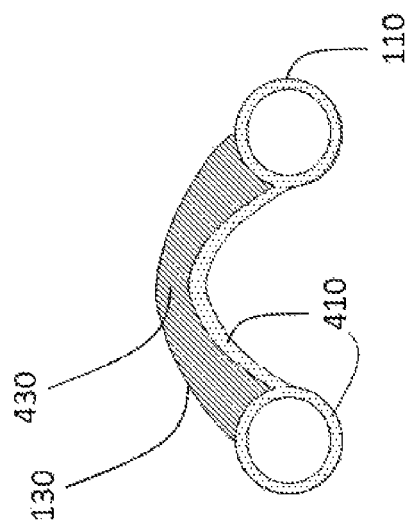
FIGS. 10A-B are schematic illustrations of a configuration of the LMA device of FIG. 1, in accordance with an application of the present invention.
Figure 10B:
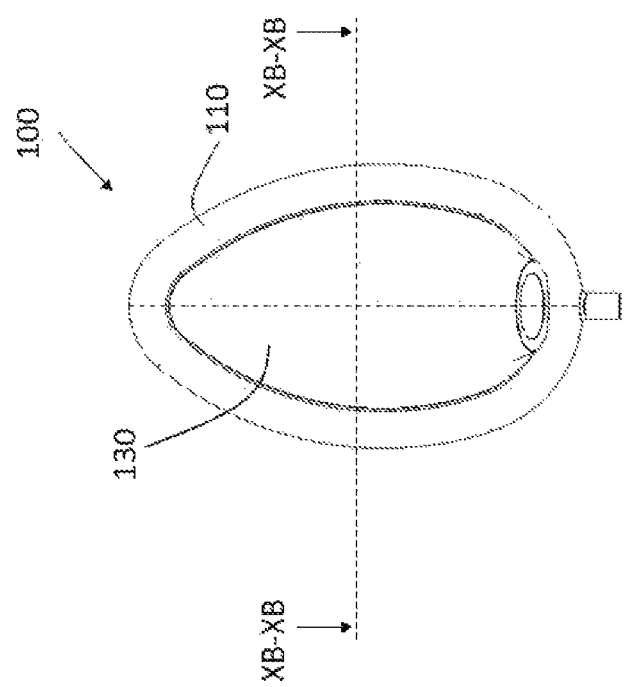

Reference is now made to FIGS. 10A-B, which are schematic illustrations of a configuration of LMA device 100, in accordance with an application of the present invention. FIG. 10A is a posterior view of LMA device 100, and FIG. 10B is a cross-sectional view taken along line XB-XB of FIG. 10A. In this configuration, backplate 130 comprises a material 430 that is stiffer (i.e., has a greater Shore value) than a material 410 of cuff 110. For example, backplate 130 may comprise two layers: a first layer of material 410 that is the same as the material of cuff 110, and a second layer of a stiffer material 430.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A laryngeal mask airway (LMA) device comprising:
    a single-layer inflatable annular cuff, which is insertable through a mouth of a patient to an inserted location within the patient, such that an anterior side of the cuff forms a seal around a laryngeal inlet of the patient upon inflation of the cuff;
    a backplate attached to the cuff; and
    an airway tube having (a) a proximal end that is configured to be disposed outside the patient's mouth when the cuff is at the inserted location, and (b) a distal end that is in fluid communication with a port of the backplate, wherein the port is open through a hollow center of the annular cuff,
    wherein the cuff, when disposed in free space, is characterized by a pressure-volume curve that represents the pressure in the cuff when inflated, from a deflated negative pressure, by different volumes of ambient-pressure air, which include a low-pressure volume that results in a low pressure of 10 cm H2O, wherein the pressure-volume curve includes:
        a low-pressure-range average rate of change over a low-pressure volume interval between 1.0 and 1.2 times the low-pressure volume,
        a medium-pressure-range average rate of change over a medium-pressure volume interval between 2.0 and 2.2 times the low-pressure volume, and
        a medium pressure at a medium volume of the cuff equal to 2.0 times the low-pressure volume,
    wherein the medium-pressure-range average rate of change is less than 0.5 times the low-pressure-range average rate of change, and
    wherein the medium pressure is between 20 and 200 cm H2O.

2. The LMA device according to claim 1, wherein the medium pressure is between 20 and 120 cm H2O.

3. The LMA device according to claim 2, wherein the medium pressure is between 20 and 70 cm H2O.

4. The LMA device according to claim 3, wherein the medium pressure is between 20 and 40 cm H2O.

5. The LMA device according to claim 1, wherein the medium-pressure-range average rate of change is equal to less than 0.4 times the low-pressure-range average rate of change.

6. The LMA device according to claim 1, wherein the pressure-volume curve does not have any local maximums at any volumes less than 3 times the low-pressure volume.

7. The LMA device according to claim 1, wherein the cuff is configured such that when disposed in free space and inflated, from the deflated negative pressure, by the low-pressure volume, further inflation of the cuff with an incremental quantity of air results in a pressure in the cuff that is less than 25 cm H2O, the incremental quantity of air having a volume, when the air is at ambient pressure, equal to 10% of the low-pressure volume.

8. The LMA device according to claim 1, wherein the cuff is configured such that when disposed in free space and inflated, from the deflated negative pressure, by the low-pressure volume, further inflation of the cuff with an incremental quantity of air results in a pressure in the cuff that is less than 35 cm H2O, the incremental quantity of air having a volume, when the air is at ambient pressure, equal to 20% of the low-pressure volume.

9. The LMA device according to claim 1, wherein the medium-pressure-range average rate of change is between 1 and 25 cm H2O.

10. The LMA device according to claim 9, wherein the medium-pressure-range average rate of change is between 5 and 20 cm H2O.

11. The LMA device according to claim 1, wherein the cuff is configured, when disposed in free space and inflated, from the deflated negative pressure, by the low-pressure volume, to have an asymmetric toroidal tubular shape.

12. The LMA device according to claim 11,
    wherein the cuff is configured, when disposed in free space and inflated, from the inflated negative pressure, by a volume of ambient-pressure air equal to 1.2 times the low-pressure volume, to have (a) a low-volume greatest external cross-sectional area and a low-volume smallest external cross-sectional area at respective locations around the cuff, and (b) a low-volume deformation ratio equal to the quotient of the low-volume greatest external cross-sectional area divided by the low-volume smallest external cross-sectional area,
    wherein the cuff is configured, when disposed in free space and inflated, from the deflated negative pressure, by a volume of ambient-pressure air equal to 3.0 times the low-pressure volume, to have (a) a high-volume greatest external cross-sectional area and a high-volume smallest external cross-sectional area at respective locations around the cuff, and (b) a high-volume deformation ratio equal to the quotient of the high-volume greatest external cross-sectional area divided by the high-volume smallest external cross-sectional area,
    wherein all of the external cross-sectional areas are measured locally perpendicular to a center line of the cuff, and
    wherein the high-volume deformation ratio equals at least 1.5 times the low-volume deformation ratio.

13. A laryngeal mask airway (LMA) device comprising:
    a single-layer inflatable annular cuff, which is insertable through a mouth of a patient to an inserted location within the patient, such that an anterior side of the cuff forms a seal around a laryngeal inlet of the patient upon inflation of the cuff;
    a backplate attached to the cuff; and
    an airway tube having (a) a proximal end that is configured to be disposed outside the patient's mouth when the cuff is at the inserted location, and (b) a distal end that is in fluid communication with a port of the backplate, wherein the port is open through a hollow center of the annular cuff,
    wherein the cuff, when disposed in free space, is characterized by a pressure-volume curve that represents the pressure in the cuff when inflated, from a deflated negative pressure, by different volumes of ambient-pressure air, which include a low-pressure volume that results in a low pressure of 10 cm H2O, wherein the pressure-volume curve includes:

a medium-pressure-range average rate of change over a medium-pressure volume interval between 2.0 and 2.2 times the low-pressure volume, wherein the medium-pressure-range average rate of change is between 1 and 25 cm H2O, and a medium pressure at a medium volume of the cuff equal to 2.0 times the low-pressure volume, wherein the medium pressure is between 20 and 200 cm H2O.

14. The LMA device according to claim 13, wherein the medium-pressure-range average rate of change is between 10 and 20 cm H2O.

15. The LMA device according to claim 13, wherein the medium pressure is between 20 and 70 cm H2O.

16. The LMA device according to claim 13, wherein the pressure-volume curve does not have any local maximums at any volumes less than 3 times the low-pressure volume.

17. The LMA device according to claim 13, wherein the cuff is configured such that when disposed in free space and inflated, from the deflated negative pressure, by the low-pressure volume, further inflation of the cuff with an incremental quantity of air results in a pressure in the cuff that is less than 25 cm H2O, the incremental quantity of air having a volume, when the air is at ambient pressure, equal to 10% of the low-pressure volume.

18. The LMA device according to claim 13, wherein the cuff is configured, when disposed in free space and inflated, from the deflated negative pressure, by the low-pressure volume, to have an asymmetric toroidal tubular shape.

19. The LMA device according to claim 18,
wherein the cuff is configured, when disposed in free space and inflated, from the deflated negative pressure, by a volume of ambient-pressure air equal to 1.2 times the low-pressure volume, to have (a) a low-volume greatest external cross-sectional area and a low-volume smallest external cross-sectional area at respective locations around the cuff, and (b) a low-volume deformation ratio equal to the quotient of the low-volume greatest external cross-sectional area divided by the low-volume smallest external cross-sectional area,
wherein the cuff is configured, when disposed in free space and inflated, from the deflated negative pressure, by a volume of ambient-pressure air equal to 3.0 times the low-pressure volume, to have (a) a high-volume greatest external cross-sectional area and a high-volume smallest external cross-sectional area at respective locations around the cuff, and (b) a high-volume deformation ratio equal to the quotient of the high-volume greatest external cross-sectional area divided by the high-volume smallest external cross-sectional area,
wherein all of the external cross-sectional areas are measured locally perpendicular to a center line of the cuff, and
wherein the high-volume deformation ratio equals at least 1.5 times the low-volume deformation ratio.

20. A method comprising:
inserting a single-layer inflatable annular cuff of a laryngeal mask airway (LMA) device through a mouth of a patient to an inserted location within the patient, such that a proximal end of an airway tube of the LMA device is disposed outside the patient's mouth, and a distal end of the airway tube is in fluid communication with a port of a backplate of the LMA device attached to the annular cuff, wherein the port is open through a hollow center of the annular cuff; and
inflating the cuff such that an anterior side of the cuff forms a seal around a laryngeal inlet of the patient,
wherein the cuff, when disposed in free space, is characterized by a pressure-volume curve that represents the pressure in the cuff when inflated, from a deflated negative pressure, by different volumes of ambient-pressure air, which include a low-pressure volume that results in a low pressure of 10 cm H2O, wherein the pressure-volume curve includes:
a low-pressure-range average rate of change over a low-pressure volume interval between 1.0 and 1.2 times the low-pressure volume,
a medium-pressure-range average rate of change over a medium-pressure volume interval between 2.0 and 2.2 times the low-pressure volume, and
a medium pressure at a medium volume of the cuff equal to 2.0 times the low-pressure volume,
wherein the medium-pressure-range average rate of change is less than 0.5 times the low-pressure-range average rate of change, and
wherein the medium pressure is between 20 and 200 cm H2O.

* * * * *